United States Patent [19]
Como Rodriguez et al.

[11] Patent Number: 5,758,655
[45] Date of Patent: Jun. 2, 1998

[54] NEEDLE DEVICE WITH IMPROVED HANDLE

[75] Inventors: Jan L. Como Rodriguez, Libertyville, Ill.; James W. Kendall, Westminster; Gregory D. Volan, Boulder, both of Colo.; Stephen Kuehn, Franklin, Wis.; T. Michael Dennehey, Arlington Heights, Ill.

[73] Assignee: Allegiance Corporation, McGaw Park, Ill.

[21] Appl. No.: 447,194

[22] Filed: May 22, 1995

Related U.S. Application Data

[63] Continuation-in-part of Ser. No. 278,418, Jul. 21, 1994, abandoned.

[51] Int. Cl.⁶ .................................................. A61B 10/00
[52] U.S. Cl. .................................... 128/749; 128/754
[58] Field of Search ................... 128/749, 750, 128/751, 752, 753, 754

[56] References Cited

U.S. PATENT DOCUMENTS

| | | | |
|---|---|---|---|
| 3,893,445 | 7/1975 | Hofsess | 128/754 |
| 4,262,676 | 4/1981 | Jamshidi . | |
| 4,266,555 | 5/1981 | Jamshidi . | |
| 4,469,109 | 9/1984 | Mehl . | |
| 4,630,616 | 12/1986 | Tretinyak | 128/753 |
| 4,655,226 | 4/1987 | Lee | 128/754 |
| 4,793,363 | 12/1988 | Ausherman et al. | 128/754 |
| 4,838,282 | 6/1989 | Strasser et al. | 128/754 |
| 4,969,870 | 11/1990 | Kramer et al. . | |
| 5,090,419 | 2/1992 | Palestrant | 128/754 |
| 5,257,632 | 11/1993 | Turkel et al. . | |
| 5,279,306 | 1/1994 | Mehl . | |
| 5,282,477 | 2/1994 | Bauer . | |
| 5,331,972 | 7/1994 | Wadhwani et al. | 128/754 |
| 5,357,974 | 10/1994 | Baldridge | 128/754 |
| 5,368,046 | 11/1994 | Scarfone et al. | 128/754 |
| 5,385,151 | 1/1995 | Scarfone et al. | 128/754 |

*Primary Examiner*—Sam Rimell
*Attorney, Agent, or Firm*—Allan O. Maki; Robert A. Stenzel

[57] ABSTRACT

A bone biopsy needle assembly which includes a handle having a proximal concave curved surface having an off-center radius producing a first relatively narrow end and a second relatively wide end of the handle. The wide end is curved to conform to the shape of a user's palm, and the narrow end forms a surface to limit lateral slippage in the direction of the user's forefinger. The handle also has a distal surface with a receiving opening. A cannula has a central lumen, with a first end extending into the receiving opening and being connected to the distal surface of the handle toward the relatively narrow end and having a second end extending distally from the handle. A removable stylet is slidably received within the lumen and has a proximal knob carried by the handle.

19 Claims, 4 Drawing Sheets

U.S. Patent    Jun. 2, 1998    Sheet 1 of 4    5,758,655
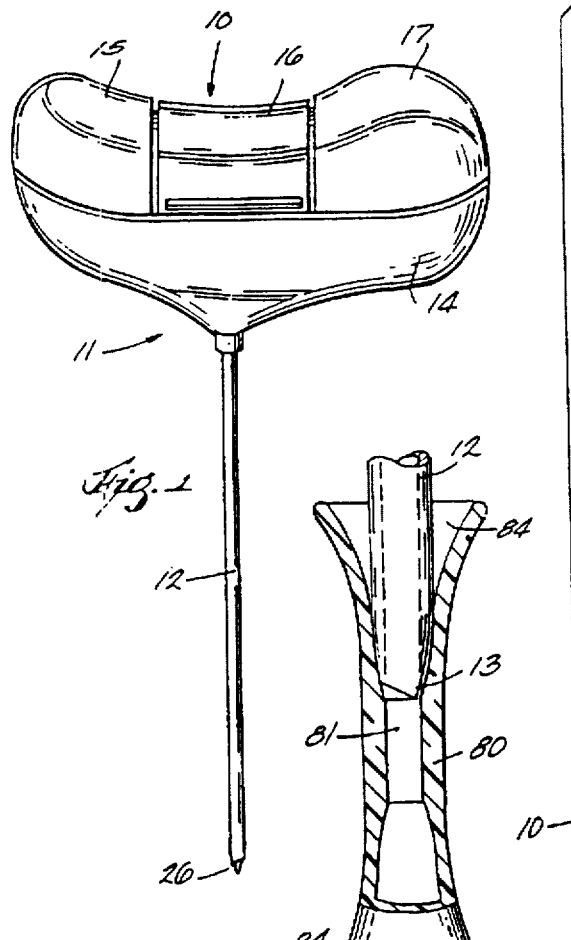
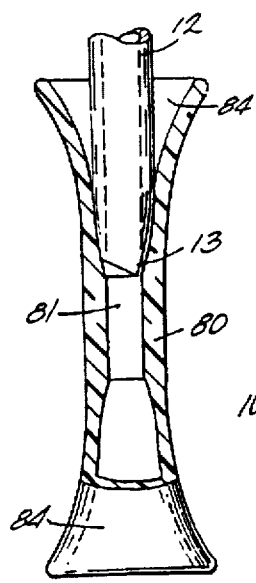
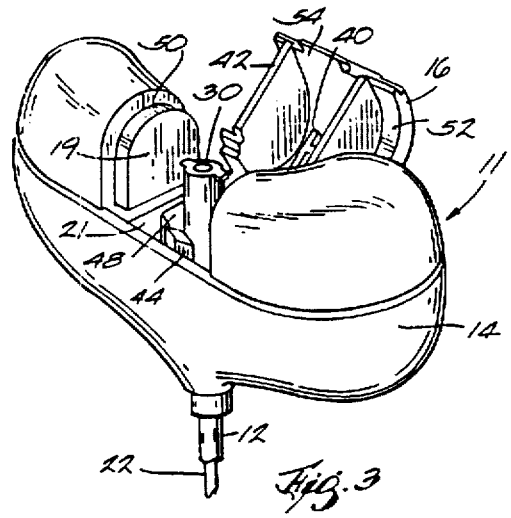
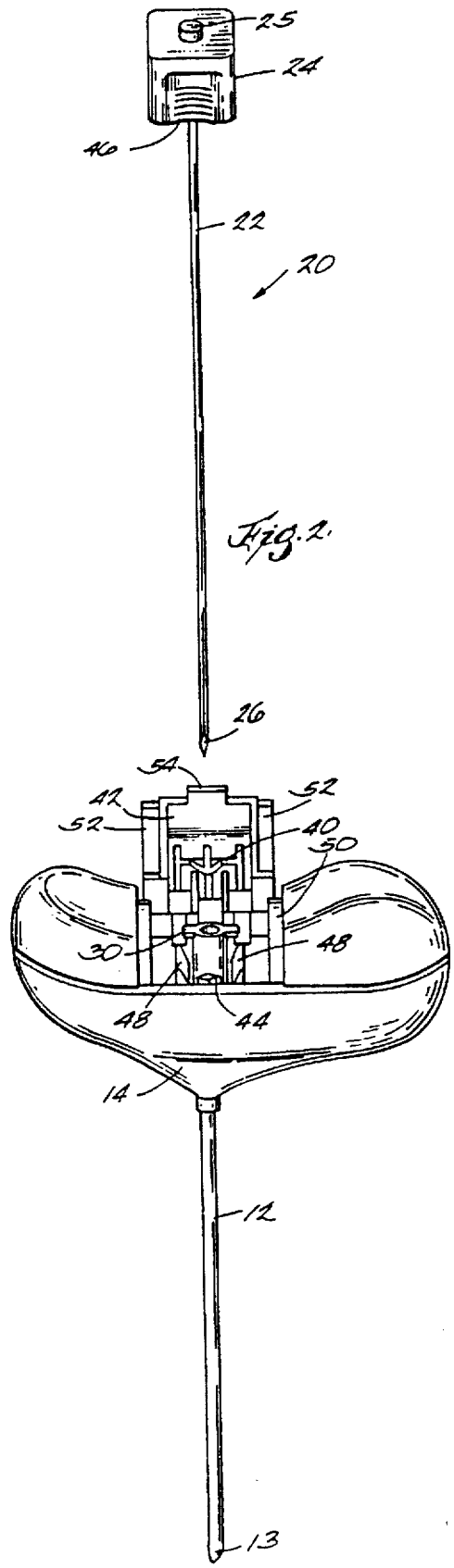

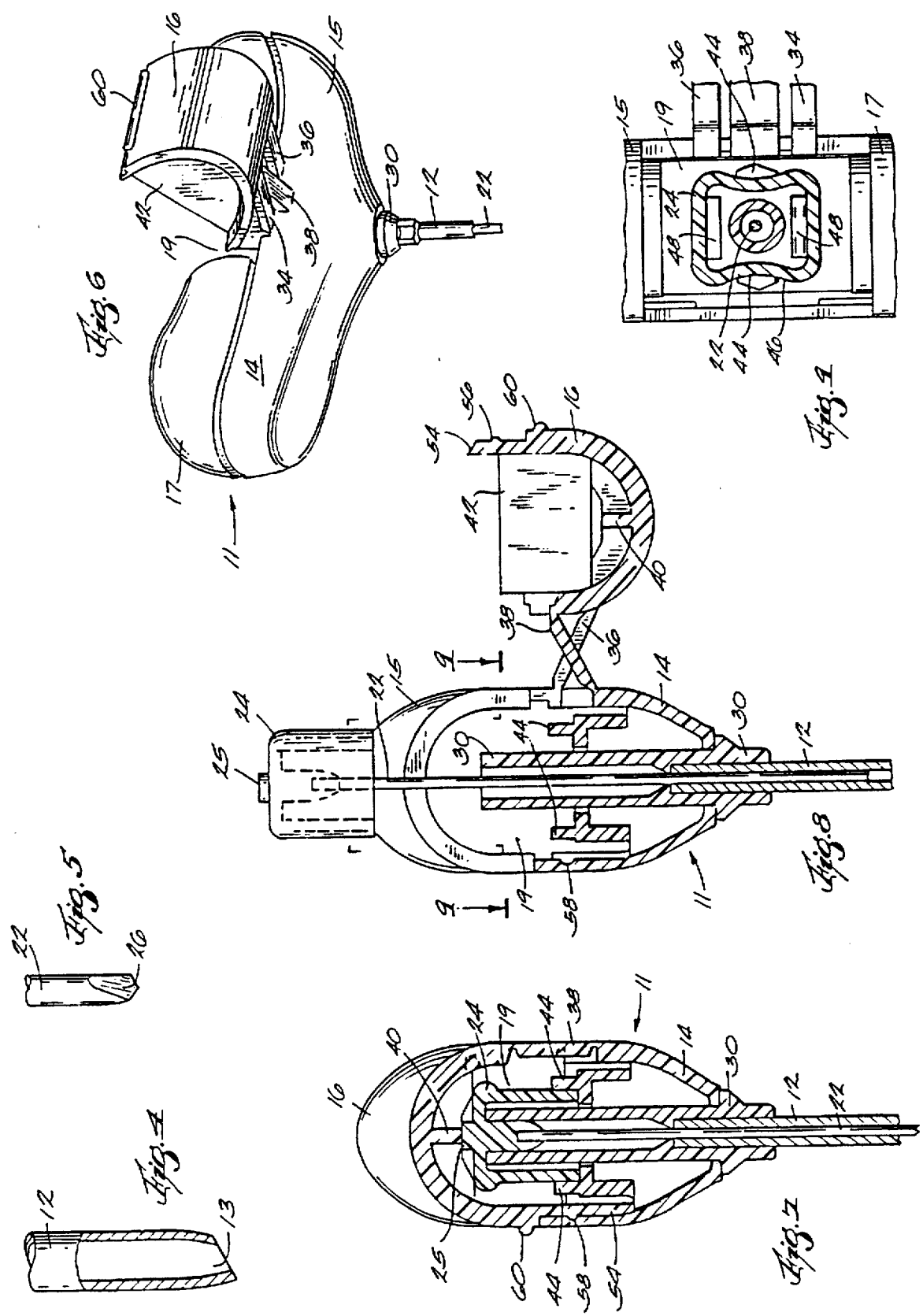

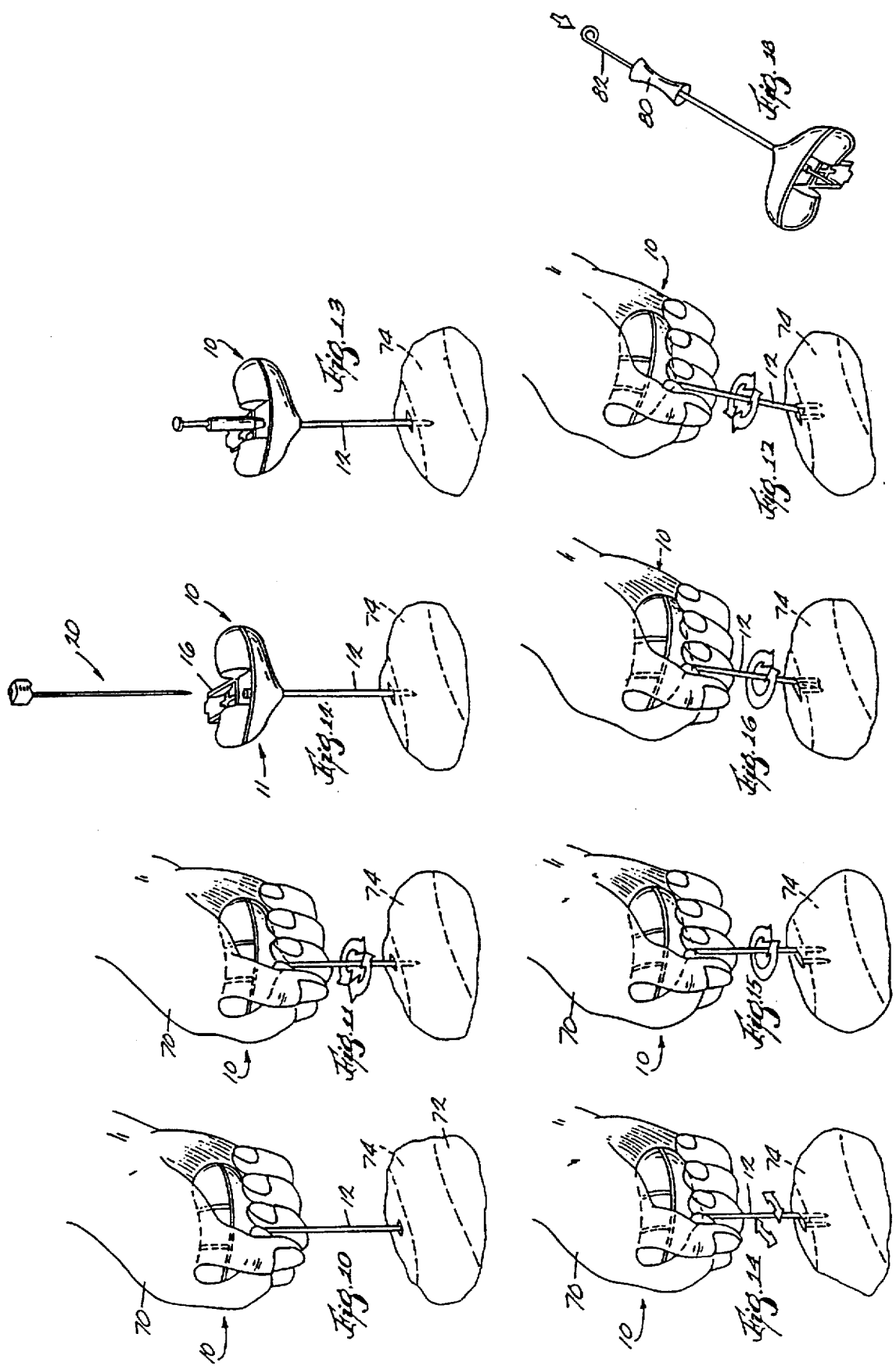

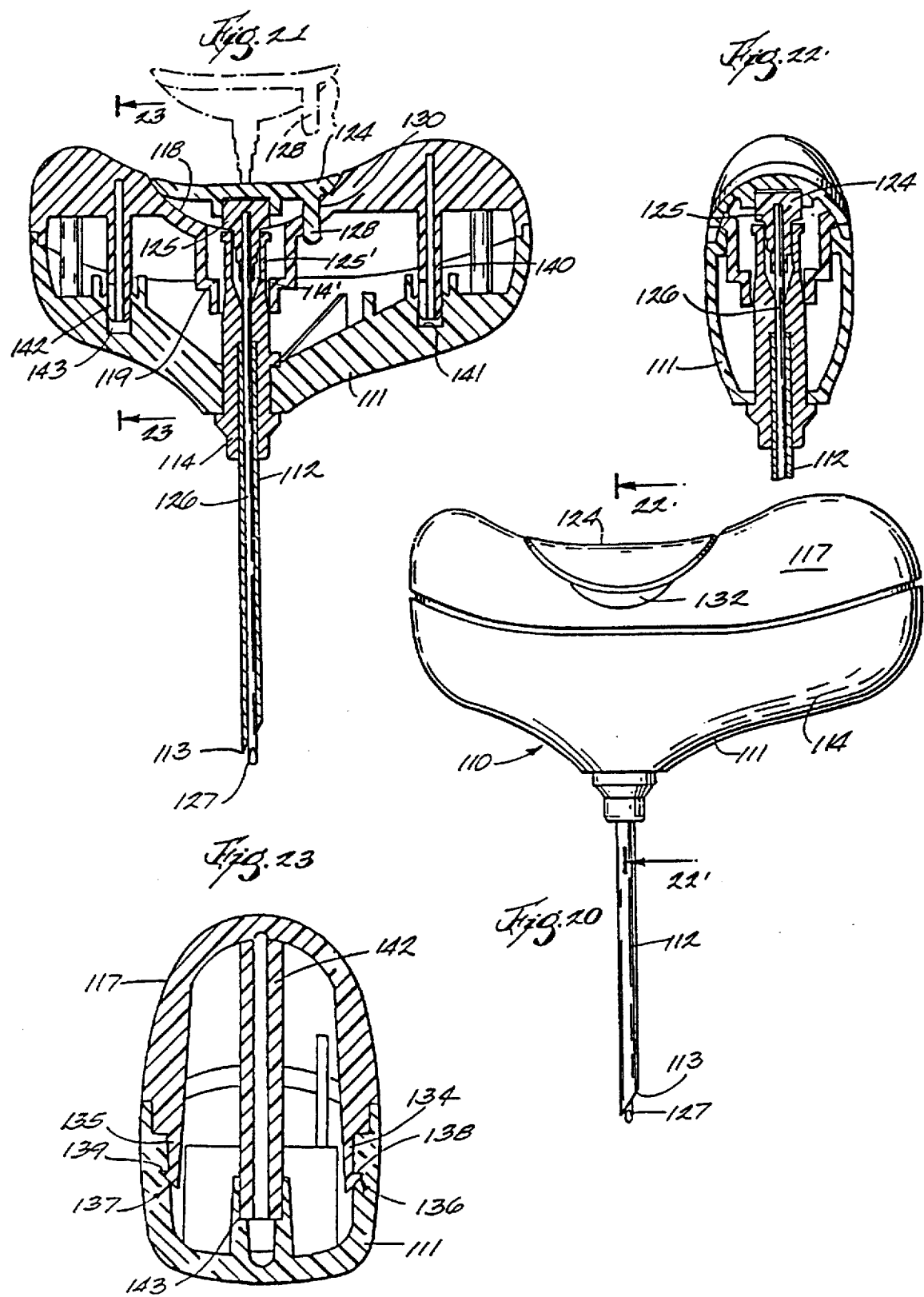

NEEDLE DEVICE WITH IMPROVED HANDLE

This is a continuation-in-part of application Ser. No. 08/278,418 filed on Jul. 21, 1994, abandoned.

TECHNICAL FIELD

The invention relates generally to the field of medical instruments, and more particularly to those instruments employed in biopsy, aspiration, and transplant procedures of body tissues and fluids such as bone marrow.

BACKGROUND OF THE INVENTION

It is frequently desirable to take biopsy samples from a patient. In bone marrow biopsy, it is always necessary to puncture the bone of a patient in order to retrieve bone marrow which normally exist only in the center of a bone.

It may be desirable to retrieve bone marrow for several different reasons. In one type of bone marrow procedure, it is desirable to retrieve a "core" of bone marrow to examine bone marrow architecture. This procedure may be useful in determining whether a patient has cancer and the extent of cancerous cells that may exist. Examining a bone marrow core typically involves an extended period of time in which the core is first prepared and then sliced into thin samples which are examined under a microscope.

Another type of bone marrow procedure involves taking an aspirate of body fluids to make a relatively rapid examination to indicate the state of a patient's disease and to aid in the diagnosis of a patient.

Finally, in other procedures, multiple aspirations of body fluids, for example bone marrow, are conducted to perform transplants such as, for example, bone marrow transplants. While each of these procedures has different goals, they all require that the body be punctured in order to access the tissue or fluid within. Thus, it is important to provide a device which enhances the ability of the user to perform the procedures such as puncturing a bone with minimal trauma to the patient.

All bone marrow biopsy, aspiration and transplant needles currently on the market have a handle with a cannula extending outwardly from the handle. The handle is used by the doctor to apply force to the cannula as the cannula punctures the bone. Such needles typically include a stylet with a sharpened tip which is inserted through the cannula and is used to initially puncture the bone. The stylet also serves to occlude the cannula while it is penetrating tissue prior to reaching the bone so that the marrow sample subsequently taken is free from unwanted tissue. The stylet is then removed and bone marrow is withdrawn from the patient by manipulating the cannula to cause bone marrow to move into the interior of the cannula. In some cases a slight suction is applied to the cannula to hold the bone marrow in place as the cannula is removed from the patient.

Bone marrow needles have traditionally been designed so that the needle is attached to the center of the handle. While many physicians feel comfortable with a centrally attached needle, it has now been discovered that it may be easier to guide a needle with a user's index finger when the needle is not centrally located on the handle of the needle assembly. It has also recently been discovered that when an off-center device is used, it is important to insure that a physician's arm, wrist, and index finger are all generally in alignment with the cannula of the needle to provide enhanced control over the needle. Examples of such devices are described in U.S. Pat. Nos. 4,469,109 and 4,838,282.

A disadvantage of most bone marrow needle assemblies currently on the market is that when the stylet is removed from the cannula, the shape of the handle typically is materially changed. For example, the bone marrow needle assembly described in U.S. Pat. No. 4,838,282 involves removing approximately half of the handle assembly when the stylet is removed from the cannula. It has recently been discovered, as part of the subject invention, that it is desirable to maintain as much as possible of the original shape of the handle after the stylet has been removed to allow a physician to more easily manipulate the cannula.

OBJECTS OF THE INVENTION

It is an object of the invention to provide a needle assembly having an ergonomically shaped offset handle to assist a physician in inserting a needle into a patient.

It is another object of the invention to provide a bone marrow needle assembly having a guide for assistance in inserting a probe into the cannula tip for removal therefrom of a biopsy specimen.

It is still another object of the invention to provide a bone marrow needle assembly having a handle design such that the shape of the handle remains essentially the same after the stylet has been removed. In accordance with a related aspect of the invention, the stylet is provided with a grasping means such as a handle or knob that is carried by the cannula handle. In one embodiment the stylet knob is received within an indentation or hollow portion in the cannula handle. In another embodiment, the handle for the stylet forms a portion of the handle upper proximal surface and is received in an indentation in the handle surface. In one embodiment, a hinged cover provides access to the hollow portion for placement and removal of the stylet. It is a further object to provide such a device wherein an improved means is provided to prevent rotation of the stylet relative to the cannula when the stylet is in place with its grasping means associated with the handle.

SUMMARY OF THE INVENTION

In a preferred embodiment of the invention the handle has a somewhat saddle shaped upper surface which, when grasped by a user, conforms to the shape of the user's palm. The saddle-shaped handle has a first relatively narrow end and a second relatively wide end. The handle also has a curved lower surface designed to be easily gripped by a user's fingers. In the preferred embodiment, the proximal end of the cannula is connected to the lower surface of the handle toward the relatively narrow end. Thus, when a user grips the handle on end, a portion of the user's index finger can be naturally applied to the cannula to guide the cannula into a patient. The cannula handle is connected to the cannula at an oblique angle that places the user's wrist and forearm in general alignment with the user's index finger and the axis of the cannula.

The invention provides a needle assembly that includes a handle having a proximal concave curved upper surface with an off-center radius and a first relatively narrow end and a second relatively wide end of the handle. The wide end is curved to conform to the shape of a user's palm, and the narrow end forms a surface to limit lateral slippage in the direction of the user's forefinger. The handle also has a distal surface with a cannula receiving opening. A cannula has a central lumen, with a first end extending into the receiving opening and being connected to the distal surface of the handle toward the relatively narrow end and having a second end extending distally from the handle. A removable stylet is slidably received within the lumen and has a proximal grasping means a knob positioned within the outer surface of the handle. In one embodiment, the grasping means may be concealed below a hinged cover and in another embodiment the grasping end is received in an indentation in the handles upper surface.

BRIEF DESCRIPTION OF THE DRAWINGS

FIG. 1 is a side elevational view of the biopsy needle assembly of this invention;

FIG. 2 is a perspective view of a biopsy needle assembly of this invention with the stylet withdrawn from the cannula;

FIG. 3 is a fragmentary perspective view of the cannula handle component of the system with the cover in the open position to expose the proximal cannula assembly;

FIG. 4 is a fragmentary enlarged view of the cannula tip with parts shown in cross-section;

FIG. 5 is a side elevational expanded fragmentary view of a stylet tip;

FIG. 6 is a perspective rear view of the cannula handle with cavity cover in the open position to show the hinge detail;

FIG. 7 is a fragmentary cross-sectional view of the handle with stylet in place shown in the closed position;

FIG. 8 is a view of the handle of FIG. 7 with the cover shown in the open position and with the stylet partially withdrawn from the cannula;

FIG. 9 is a fragmentary cross-sectional view taken along line 9—9 of FIG. 8;

FIG. 10 is a fragmentary perspective view illustrating the manner in which the device of this invention is grasped and illustrating the initial entry into a body;

FIG. 11 shows a view of the device of FIG. 10 as it is penetrating a bone;

FIG. 12 is a view of the device of FIG. 10 after the marrow cavity of the bone has been entered and showing the withdrawal of the stylet;

FIG. 13 shows the device of FIG. 10 during aspiration of material utilizing a syringe;

FIGS. 14–17 illustrates the use of the device of FIG. 10 to reenter the bone cavity to obtain a biopsy specimen;

FIG. 18 illustrates the use of a probe guide and probe to remove a biopsy specimen from the cannula;

FIG. 19 is a side view of the probe guide and fragmentary cannula tip with parts broken away and in section;

FIG. 20 is a side elevational view of an embodiment of the invention wherein the stylet knob is received in an indentation on an outer surface of the handle;

FIG. 21 is a side elevational cross sectional view of the embodiment of FIG. 20 showing, in phantom lines, the stylet knob removed from the handle;

FIG. 22 is a cross sectional view taken along the line 22—22 of FIG. 20; and

FIG. 23 is a sectional view taken along line 23—23 of FIG. 20.

DETAILED DESCRIPTION OF PREFERRED EMBODIMENTS

Referring more particularly to the drawings there is seen an embodiment of a biopsy needle assembly 10 which includes a hollow cannula 12 having an open, sharpened distal end 13, and being attached to a handle 11 at its proximal end. Handle 11 is provided with a cover 16 that pivots open to the position seen in FIGS. 2 and 3 to expose a gap or hollow portion 19 of the handle into which the cannula hub 30, which is secured to the proximal end of cannula 12, is open. Ends 15 and 17 of handle 14 extend laterally and have central axes that are attached to cannula 12 at an oblique angle with respect to the cannula axis so as to form a saddle shaped configuration that will conform to the hand of a user. End 15 which is designed to be grasped by the forefinger and thumb of the user is of a smaller cross-section and shorter than end 17 which is designed to engage the user's palm.

Handle 11 includes a bottom portion 14, to which a cover 16 is hinged. Upper lateral end portions of the handle 15 and 17 are preferably formed from a single molded piece connected together by means of a flat connecting portion 21 that forms a bottom to a hollow portion 19 of the handle assembly. The handle can, thus, conveniently be formed from two molded parts. A hollow tubular cannula hub 30 is molded to the proximal end of cannula 12 and serves to secure the cannula 12 to handle 11 by tight frictional engagement of hub 30 or snap fit of hub in an aperture through the distal surface of bottom 14 of the handle 11. Hub 30 extends upwardly into hollow handle portion 19. The hollow interior of cannula hub 30 is connected in fluid flow communication with the hollow interior of cannula 12 as can best be seen in FIGS. 7 and 8. Cannula hub 30, as well as any other parts coming into contact with body fluids, are preferably formed from a polystyrene terpolymer of acrylonitrile, butadiene and styrene (ABS) or, alternatively, a polycarbonate polymer.

A stylet 20 having a shaft 22 and a grasping means or knob 24 fits within the handle 11 with the distal end 26 of the stylet extending beyond the distal end 13 of cannula 12. Knob 24 is provided with a proximal projection 25 in order to provide additional compression resistance to the knob and to provide a surface against which internal ribs 40 of the handle are supported during use of the instrument.

Cover portion 16 is hingedly connected to the bottom part 14 of handle 11 by means of living hinges 34, 36 and 38. In the preferred configuration of these hinges best seen in FIGS. 6 and 8, it will be noted that the outermost hinges 34 and 36 are pivoted at a higher point on the base portion 14 of the handle than is the inner hinge 38. The upper end of central living hinge 38 is also hinged nearer the perimeter of cover 16. This causes rotational pivoting of cover 16 as it is opened, causing it to pivot out of the way of knob 14 more rapidly than would otherwise be the case. This hinge arrangement also holds the cover in a relatively elevated position as seen in FIG. 8 when open.

The handle components 14, 15, 16 and 17 are all preferably provided with ribs 40 to provide structural integrity and light weight to the handle 11. These components are all preferably formed from a polyolefin such as a high density polyethylene, polypropylene, or a polyester or similar thermoplastic polymeric material. The cover 16 is preferably provided with end walls 42 that provide a chamber surrounding knob 24 when the cover is in the closed position.

The base portion 21 is provided with upwardly extending projections 44 and 48. Projections 44 on the forward and rearward sides of the handle closely engage curved indentations 46 in the lower part of knob 24. Knob 24 also fits tightly over the outside of projections 48, thus forming a structure that prevents relative rotation of stylet 22 and cannula 12 even when substantial force is applied to the needle assembly by the physician.

Lip 54 of cover 16 fits within the bottom part of handle 14 as can be seen in FIG. 7. An indentation 58 is provided in lower handle portion 14 to matingly receive a projection 56 of the cover in order to retain the cover in a closed position. A ridge 60 is provided to form a surface to be grasped in order to open cover 16.

The procedure for use of the instrument of this invention is shown in FIGS. 10–19. As seen in FIG. 10, the needle, grasped in physician's hand 70, is introduced through an incision, through soft tissue 72 toward and into contact with bone structure 74, usually the posterior iliac spine. The needle is advanced into the marrow cavity by alternating 45° clockwise/counter-clockwise rotation. The cover 16 is then opened as seen in FIG. 12 and the stylet removed from the cannula. For sample aspiration syringe 76 is then attached to the cannula hub 30, which is preferably provided with a luer fitting for that purpose. Negative pressure is applied by quickly withdrawing the syringe plunger to remove an aspirated specimen.

The biopsy procedure is illustrated in FIG. 15–19, wherein another penetration to the marrow cavity is made, and after removal of the stylet, the cannula is advanced into the marrow cavity to obtain a specimen. Optionally, a knob (not shown) similar to the stylet knob 24 is included with the needle assembly and is placed in the handle to fill the space provided for knob 24. The specimen is detached from surrounding tissue by redirection and rotation of the cannula a number of times in each direction. The specimen is removed from the cannula as shown in FIG. 19 by introducing a probe 82 through the distal end of the cannula utilizing the probe guide 80 to insure easy insertion of the probe into the lumen of the cannula. The biopsy specimen is then pushed up into the proximal end of the cannula and through the cannula hub.

As seen, probe guide 80 is preferably a molded plastic shape in the form of a generally hourglass configuration. A cylindrical opening extends through the length of said elongated dimension of the guide between its ends. The cylindrical elongated opening has a diameter substantially equal to that of said interior lumen of cannula 12. Preferably there is at each end of the opening a flared outward enlargement for alignment with the distal end of the cannula and for forming a guide for insertion of a probe into said distal end of the cannula for removal of a biopsy specimen.

In the embodiment of FIGS. 20–22, a needle assembly generally indicated at 110 includes a hollow cannula 112 having an open sharpened distal end 113, and being attached to a handle 111 at its proximal end. Handle 111 is provided with a recessed portion 118 that receives a stylet grasping means or knob 124. A solid stylet 126 has distal tip 127 and a first end affixed to the knob 124. Knob 124 is molded to stylet 126 and knob 124 has an outer somewhat saddle-shaped surface conforming to the shape of the handle 111 in order to provide a smooth exterior surface for the assembly.

A pin 128 integral with knob 124 is received in a mating opening 130 in recess 118 of handle 111 and serves to locate knob 124 in a desired rotational orientation and to prevent relative rotation between cannula 112 and stylet 126. Stylet needle 126 has a sharpened distal tip 127 which is flush with the distal tip 113 of cannula 112. Stylet 126 serves to occlude cannula 112, preventing it from filling with bone chips or unwanted tissue fragments. A finger receiving recess 132 is provided in the proximal surface of handle 111 to facilitate removal of knob 124 from recess 118.

In the embodiment shown, stylet 126 has a hub 125 affixed thereto by means such as being integrally molded to the proximal end. Cannula 112 has hub 114 affixed thereto by means such as been integrally molded to the proximal end. In this embodiment, the hubs 114 and 125 serve to retain the cannula and stylet in fixed relationship to one another prior to assemble with the handle 111 and knob 124, respectively. Hub 125 also may include a key as shown at 125' in FIG. 22 which fits into a recession 114, in hub 114. This assembly allows simultaneous guiding of the tips 113 and 127 prior to final assembly with the handle and knob portions.

The handles 11 and 111 may comprise an upper portion 17,117, respectively, and a bottom portion 14, 114, respectively. The upper and bottom portions preferably are hollow molded members that may advantageously be snap fitted together as shown for example in FIGS. 21–23. Thus, as best seen in FIG. 23, the upper portion 117 includes a pair of depending legs 134,135 each having an outwardly projecting tines 136,137, respectively. The bottom portion 114 includes indentations 138,139 on opposite sides which are positioned to receive tines 136, 137, respectively, in a snap fit interlocking arrangement whereby the upper and bottom portions are easily locked together. Pairs of connectors are advantageously arranged on opposite sides of posts 140 and 142, respectively. During assembly of parts 114 and 117, posts 140 and 142 are received in indentations 141 and 143, respectively. This arrangement has been found to provide an interference fit that keeps the portions secure and stable relative to one another.

What is claimed is:

1. A biopsy needle assembly having a handle with a distal surface from which a needle extends distally and a proximal surface for engagement of the handle by the palm of a user, said proximal surface having a concave curved proximal extremity having a first end and a second end, said first end being narrow relative to said second end, the second, wide end being curved to conform to the shape of a user's palm, and the narrow first end forming a surface to limit lateral slippage in the direction of the user's forefinger, said concave surface having a center which is displaced from said needle toward said wide end, the distal surface having a receiving opening;

a cannula having a central lumen, the cannula having a first end extending into said receiving opening and being connected to said distal surface of said handle toward said relatively narrow end and having a second end extending distally from said handle opening; and a removable stylet adapted to be fitted within said lumen, said stylet having first and second ends, said first end of stylet having a knob which forms a proximal grasping means, said proximal knob adapted to be carried by said handle and conforming to an indentation in said handle, said stylet, in use, being positioned within and extending through the length of said cannula lumen.

2. A needle assembly according to claim 1 wherein said distal surface is of a generally convex shape and said opening extends through said distal surface.

3. An assembly according to claim 1 wherein said handle comprises a hollow molded polymeric material.

4. An assembly according to claim 3 wherein said stylet knob is positioned within said hollow handle.

5. An assembly according to claim 3 wherein said stylet knob is received in an indentation in said proximal surface of said handle.

6. An assembly according to claim 5 wherein said indentation includes a portion wider than said knob, which facilitates manual grasping of said knob.

7. An assembly according to claim 3 wherein said hollow handle is formed of two parts that are snap fitted together.

8. A biopsy needle assembly, comprising:

a handle having a proximal concave curved surface having first and second raised ends on opposite sites of a depressed center which is displaced toward one end of said handle thus forming a first relatively narrow end and a second end which is relatively wide relative to said first end, the wide end being curved to conform to the shape of a user's palm, and the narrow end forming a surface to limit lateral slippage in the direction of the user's forefinger, the handle also having a distal surface, the distal surface having a receiving opening;

a cannula having a central lumen, the cannula having a first end extending into said receiving opening and being connected to said distal surface of said handle toward said relatively narrow end and having a second end extending distally from said handle; and a removable stylet to be fitted within said lumen having first and second ends, said stylet having a proximal knob positioned within a hollow part of said handle and a shaft positioned within and extending through the length of said cannula lumen.

9. An assembly according to claim 8 wherein said handle comprises a hollow molded polymeric shape.

10. A biopsy needle assembly having a handle with a distal surface from which a biopsy aspiration needle extends distally and a proximal surface for engagement of the handle by the palm of a user, said proximal surface having a concave curved proximal extremity having a first raised relatively narrow end and a second raised relatively wide end relative to said first end, the wide end being curved to conform to the shape of a user's palm, and the narrow end forming a surface to limit lateral slippage in the direction of the user's forefinger, said concave surface having a center which is displaced from said needle toward said wide end and having a stylet knob receiving indentation, the distal surface having a cannula receiving opening;

a cannula having a central lumen, the cannula having a first end extending into said receiving opening and being connected to said distal surface of said handle toward said relatively narrow end and having a second end extending distally from said handle; and a removable stylet fitted within said lumen having first and second ends, said stylet having a proximal knob carried by said handle, being fitted in said indentation and a shaft positioned within and extending through the length of said cannula lumen.

11. An assembly according to claim 10 wherein said knob is provided with means to prevent relative rotation between said knob and said handle.

12. An assembly according to claim 11 wherein said means to prevent rotation comprises a pin integral with said knob, and the proximal surface of said handle comprises an opening for receiving said pin.

13. An assembly according to claim 10 wherein said knob has a saddle-shaped proximal surface.

14. An assembly according to claim 10 wherein said stylet has a sharpened end that is flush with said distal end of said cannula.

15. An assembly according to claim 1 wherein said stylet, when assembled in said cannula, is provided with a sharpened end that extends distally beyond the distal end of said cannula.

16. An assembly according to claim 9 wherein said handle comprises at least two parts that snap fit together and wherein internal alignment posts are provided for guiding said parts into alignment with each other.

17. An assembly according to claim 16 wherein said snap fitting is provided by interfitting projections and recesses on said two parts.

18. An assembly according to claim 17 wherein said projections on one of said parts include at least one laterally extending tine on at least one of said projections which interlocks with the other one of said parts.

19. An assembly according to claim 10 wherein said stylet comprises a hub molded thereon and said knob is fitted over said hub.

* * * * *